United States Patent
Fujimori

(10) Patent No.: US 10,492,672 B2
(45) Date of Patent: Dec. 3, 2019

(54) IMAGE PICK UP UNIT FOR ENDOSCOPE AND ENDOSCOPE

(71) Applicant: OLYMPUS CORPORATION, Tokyo (JP)

(72) Inventor: Noriyuki Fujimori, Suwa (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/181,445

(22) Filed: Nov. 6, 2018

(65) Prior Publication Data

US 2019/0082944 A1    Mar. 21, 2019

Related U.S. Application Data

(63) Continuation of application No. PCT/JP2016/065282, filed on May 24, 2016.

(51) Int. Cl.
*A61B 1/05* (2006.01)
*H04N 5/225* (2006.01)
(Continued)

(52) U.S. Cl.
CPC ............... *A61B 1/05* (2013.01); *A61B 1/00* (2013.01); *A61B 1/00096* (2013.01);
(Continued)

(58) Field of Classification Search
CPC ...... H04N 5/2251; H04N 5/2254; A61B 1/05; A61B 1/00096; A61B 1/00163; A61B 1/00186; G02B 23/2407
See application file for complete search history.

(56) References Cited

U.S. PATENT DOCUMENTS

2004/0130640 A1   7/2004 Fujimori
2006/0044450 A1*  3/2006 Wolterink ............ G02B 13/006
                                                   348/340
(Continued)

FOREIGN PATENT DOCUMENTS

EP    1577950 A1    9/2005
EP    2202796 A1    6/2010
(Continued)

OTHER PUBLICATIONS

International Search Report dated Jul. 19, 2016 issued in PCT/JP2016/065282.

*Primary Examiner* — Daniel M Pasiewicz
(74) *Attorney, Agent, or Firm* — Scully, Scott, Murphy & Presser, P.C.

(57) ABSTRACT

An image pickup unit includes a first element with a first flat glass, a second element with a second flat glass, a first spacer configured to define a distance between the first element and the second element, an image pickup device, and a second spacer configured to define a distance between the second element and the image pickup device, wherein no resin lens is disposed on a light incidence surface of the first flat glass, a resin lens with a negative power is disposed on a surface opposing the light incidence surface, a resin lens with a positive power is disposed on a second flat glass, the image pickup unit has side surfaces covered with a sealing member composed of an inorganic material, a brightness aperture is disposed between the first element and the second element, and an path space is a sealed space.

7 Claims, 5 Drawing Sheets

(51) Int. Cl.
  *A61B 1/00*   (2006.01)
  *G02B 23/24*  (2006.01)
  *A61B 1/04*   (2006.01)
  *A61B 1/005*  (2006.01)

(52) U.S. Cl.
  CPC ...... *A61B 1/00163* (2013.01); *A61B 1/00186* (2013.01); *A61B 1/04* (2013.01); *G02B 23/2407* (2013.01); *H04N 5/2251* (2013.01); *H04N 5/2254* (2013.01); *A61B 1/005* (2013.01); *H04N 2005/2255* (2013.01)

(56) References Cited

U.S. PATENT DOCUMENTS

| | | | |
|---|---|---|---|
| 2009/0206431 A1* | 8/2009 | Bolken | G02B 7/02 257/432 |
| 2009/0213262 A1* | 8/2009 | Singh | G02B 7/021 348/340 |
| 2010/0053318 A1 | 3/2010 | Sasaki | |
| 2010/0157446 A1 | 6/2010 | Sander et al. | |
| 2010/0321564 A1* | 12/2010 | Feldman | G02B 9/12 348/374 |
| 2011/0063428 A1 | 3/2011 | Sonnenschein et al. | |
| 2012/0134028 A1 | 5/2012 | Maruyama | |
| 2012/0242814 A1* | 9/2012 | Kubala | B26F 1/38 348/76 |
| 2013/0163101 A1* | 6/2013 | Fukuta | G02B 9/08 359/794 |

FOREIGN PATENT DOCUMENTS

| | | |
|---|---|---|
| EP | 2466341 A1 | 6/2012 |
| EP | 2621158 A2 | 7/2013 |
| EP | 2621159 A2 | 7/2013 |
| JP | S60-73610 A | 4/1985 |
| JP | S63-308954 A | 12/1988 |
| JP | H11-023980 A | 1/1999 |
| JP | 2001-292354 A | 10/2001 |
| JP | 2004-207461 A | 7/2004 |
| JP | 2007-187864 A | 7/2007 |
| JP | 2009-240634 A | 10/2009 |
| JP | 2010-011230 A | 1/2010 |
| JP | 2010-056292 A | 3/2010 |
| JP | 2010-152358 A | 7/2010 |
| JP | 2011-081354 A | 4/2011 |
| JP | 2011-085625 A | 4/2011 |
| JP | 2012-018993 A | 1/2012 |
| JP | 2013-504400 A | 2/2013 |
| JP | 2013-125059 A | 6/2013 |
| WO | WO 2004/059740 A1 | 7/2004 |
| WO | WO 2011/019067 A1 | 2/2011 |
| WO | WO 2011/033513 A1 | 3/2011 |

* cited by examiner

IMAGE PICK UP UNIT FOR ENDOSCOPE AND ENDOSCOPE

CROSS REFERENCE TO RELATED APPLICATION

This application is a continuation application of PCT/JP2016/065282 filed on May 24, 2016, the entire contents of which are incorporated herein by this reference.

BACKGROUND OF INVENTION

1. Field of the Invention

The present invention relates to an image pickup unit for endoscope including a wafer-level stacked body disposed in a rigid distal end portion of an endoscope, and an endoscope having an image pickup unit for endoscope including a wafer-level stacked body disposed in its rigid distal end portion.

2. Description of the Related Art

It is important for an image pickup unit for endoscope disposed in a rigid distal end portion of an endoscope to decrease in diameter for minimal invasiveness.

Japanese Patent Application Laid-Open Publication No. 2012-18993 discloses an image pickup module composed of a wafer-level stacked body as a method for efficiently manufacturing an image pickup unit having a small diameter. The image pickup module is manufactured by bonding a lens wafer including a plurality of lenses and an image pickup wafer including a plurality of image pickup devices, followed by cutting the bonded wafers into wafer level stacked bodies as individual pieces.

On the other hand, Japanese Patent Application Laid-Open Publication No. 2007-187864 discloses a hybrid lens having a lens made of resin disposed in its lens base material made of glass.

SUMMARY OF THE INVENTION

An image pickup unit for endoscope according to an embodiment of the present invention includes a first optical element configured to use as a base a first parallel flat glass having a first main surface as a light incidence surface and a second main surface opposing the first main surface, a second optical element configured to use as a base a second parallel flat glass having a third main surface and a fourth main surface opposing the third main surface, a first spacer configured to define a distance between the first optical element and the second optical element, an image pickup device including a light receiving section having a light receiving surface and a rear surface opposing the light receiving surface, the light receiving section being configured such that an object image is fixated on the light receiving surface, and a second spacer configured to define a distance between the second optical element and the image pickup device, in which the first optical element, the first spacer, the second optical element, and the second spacer, and the image pickup device are stacked, where respective outer shapes in cross section in a direction perpendicular to an optical axis of the first optical element, the first spacer, the second optical element, and the second spacer are the same in size; no resin lens is disposed on the first main surface of the first parallel flat glass and a resin lens with a negative power is disposed on the second main surface of the first parallel flat glass; a resin lens with a positive power is disposed on at least one of the third main surface and the fourth main surface of the second parallel flat glass; the image pickup unit for endoscope further has a side surface covered with a sealing member composed of an inorganic material, a brightness aperture is disposed between the first optical element and the second optical element, and an optical path space of the image pickup unit for endoscope is a sealed space.

An endoscope according to another embodiment of the present invention includes an image pickup unit for endoscope in a rigid distal end portion of an insertion section, the image pickup unit for endoscope including a first optical element configured to use as a base a first parallel flat glass having a first main surface as a light incidence surface and a second main surface opposing the first main surface, a second optical element configured to use as a base a second parallel flat glass having a third main surface and a fourth main surface opposing the third main surface, a first spacer configured to define a distance between the first optical element and the second optical element, an image pickup device including a light receiving section having a light receiving surface and a rear surface opposing the light receiving surface, the light receiving section being configured such that an object image is formed on the light receiving surface, and a second spacer configured to define a distance between the second optical element and the image pickup device, in which the first optical element, the first spacer, the second optical element, and the second spacer, and the image pickup device are stacked, where respective outer shapes in cross section in a direction perpendicular to an optical axis of the first optical element, the first spacer, the second optical element, and the second spacer are the same in size; no resin lens is disposed on the first main surface of the first parallel flat glass and a resin lens with a negative power is disposed on the second main surface of the first parallel flat glass; a resin lens with a positive power is disposed on at least one of the third main surface and the fourth main surface of the second parallel flat glass; the image pickup unit for endoscope further has a side surface covered with a sealing member composed of an inorganic material, a brightness aperture is disposed between the first optical element and the second optical element, and an optical path space of the image pickup unit for endoscope is a sealed space.

DETAILED DESCRIPTION OF THE PREFERRED EMBODIMENT(S)

<Configuration>

Figure 1:
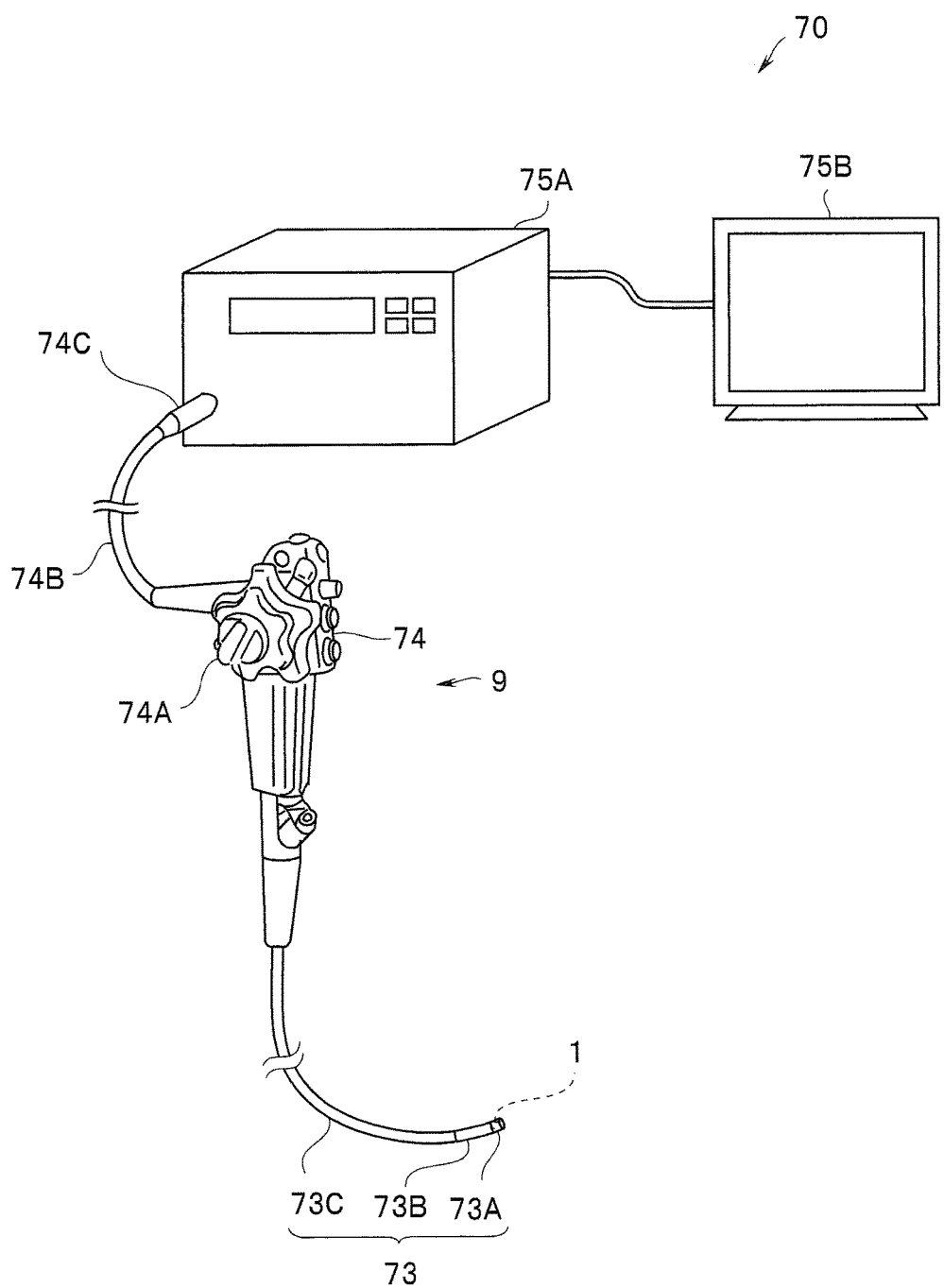
FIG. 1 is a perspective view of an endoscope system including an endoscope according to an embodiment.

As illustrated in FIG. 1, an image pickup unit for endoscope 1 (hereinafter referred to as an "image pickup unit 1") is disposed in a rigid distal end portion 73A of an insertion section 73 in an endoscope 9.

Note that in the following description, drawings based on an embodiment are schematic, and a relationship between a thickness and a width of each of sections, a proportion of respective thicknesses of the sections, a relative angle, and the like respectively differ from actual ones. Among the drawings, sections, which differ in dimensional relationship and proportion, may be respectively included. Illustration of some of components may be omitted.

The endoscope 9 includes the insertion section 73, a grasping section 74 disposed on the side of a proximal end portion of the insertion section 73, a universal code 74B extending from the grasping section 74, and a connector 74C disposed on the side of a proximal end portion of the universal code 74B. The insertion section 73 includes the rigid distal end portion 73A in which the image pickup unit 1 is disposed, a bending portion 73B extending toward a proximal end of the distal end portion 73A and being bendable for changing a direction of the distal end portion 73A, and a flexible portion 73C extending toward a proximal end of the bending portion 73B.

An angle knob 74A which rotates as an operation section for an operator to operate the bending portion 73B is disposed in the grasping section 74.

The universal code 74B is connected to a processor 75A via the connector 74C. The processor 75A controls an entire endoscope system 70 while performing signal processing for an image pickup signal outputted by the image pickup unit 1 to output the image pickup signal as an image signal. A monitor 75B displays the image signal outputted by the processor 75A as an endoscope image. Note that the endoscope 9 is a flexible mirror, but the endoscope 9 may be a rigid mirror if the endoscope 9 has a bending portion. That is, a flexible portion or the like is not an essential component of the endoscope according to the present embodiment.

In the image pickup unit 1, only a first main surface 10SA of a first optical element 10 is a light incidence surface exposed to the outside, and a second main surface 10SB of the first optical element 10, respective main surfaces of other optical elements, and respective side surfaces of all the optical elements are not exposed to the outside, as described below.

Figure 2:
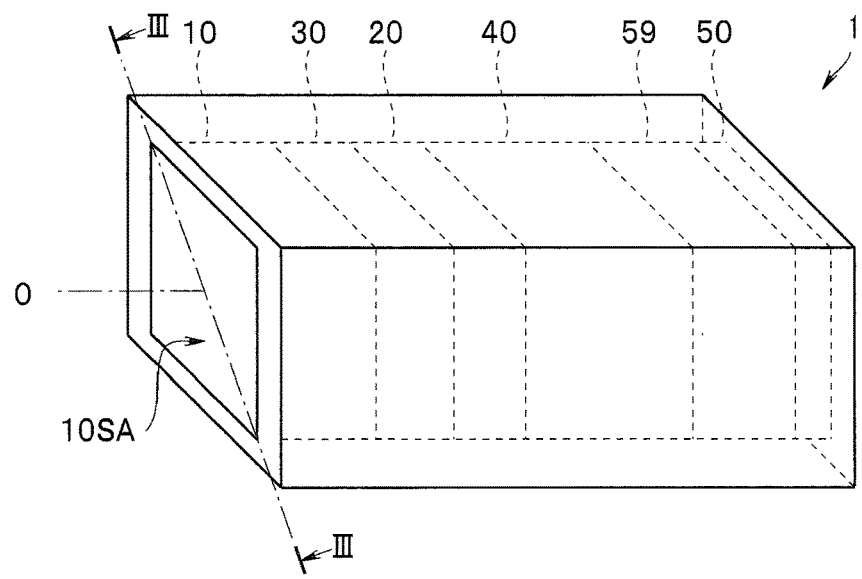
FIG. 2 is a perspective view of an image pickup unit according to the present embodiment.
Figure 3:
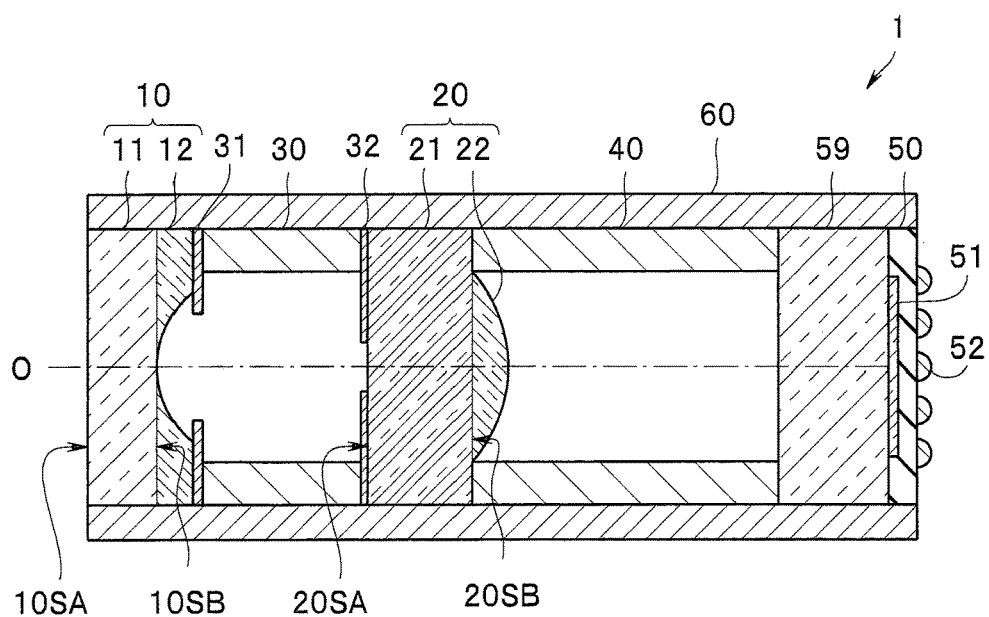
FIG. 3 is a cross-sectional view along a line III-III illustrated in FIG. 2 of the image pickup unit according to the present embodiment.
Figure 4:
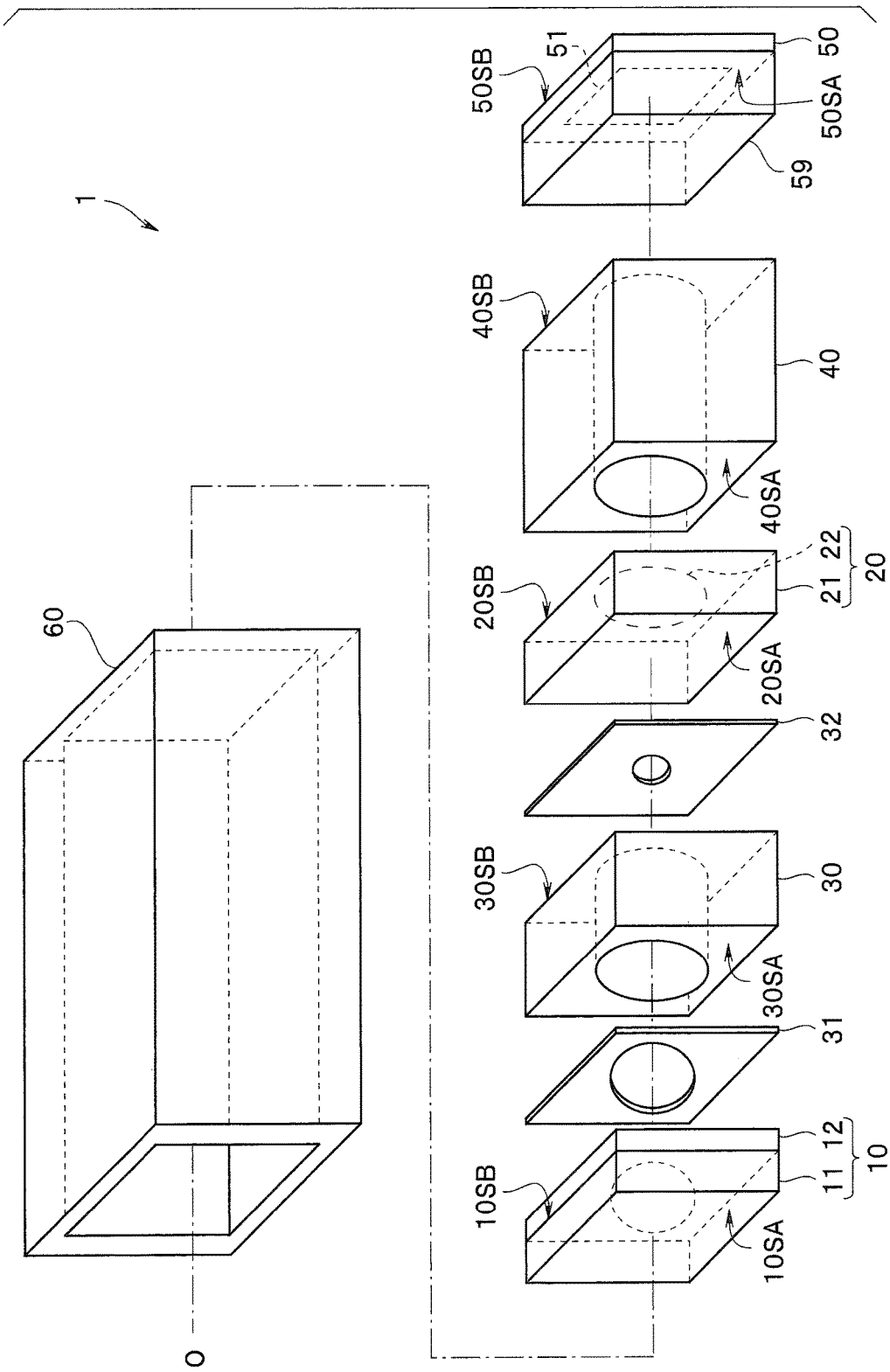
FIG. 4 is an exploded view of the image pickup unit according to the present embodiment.

That is, as illustrated in FIGS. 2 to 4, the image pickup unit 1 includes the first optical element 10, a second optical element 20, a first spacer 30, a second spacer 40, and an image pickup device 50 to which a cover glass 59 has adhered, and a side surface (outer surface) of the image pickup unit 1 is covered with a sealing member 60 composed of an inorganic material.

The first optical element 10 uses as a base a first parallel flat glass 11 having the first main surface 10SA as a light incidence surface disposed to be exposed to the outside at a distal end of the rigid distal end portion 73A and the second main surface 10SB opposing the first main surface 10SA. The second optical element 20 uses as a base a second parallel flat glass 21 having a third main surface 20SA and a fourth main surface 20SB opposing the third main surface 20SA. The first spacer 30 defines a distance between the first optical element 10 and the second optical element 20.

The image pickup device 50 has a light receiving surface 50SA and a rear surface 50SB opposing the light receiving surface 50SA, and includes a light receiving section 51 composed of a CCD or the like, on which an object image is formed, on the light receiving surface 50SA. An external electrode 52 connected to the light receiving section 51 is disposed on the rear surface 50SB via a through wiring (not illustrated). The image pickup device 50 receives a driving signal and transmits an image pickup signal via a wiring connected to the external electrode 52.

The second spacer 40 defines a distance between the second optical element 20 and the image pickup device 50. The first spacer 30 and the second spacer 40 are each composed of a metal or silicon, for example, composing a sidewall constituting a space (through hole) as an optical path.

The first optical element 10, the first spacer 30, the second optical element 20, the second spacer 40, and the image pickup device 50 are rectangles respective outer shapes in cross section in a direction perpendicular to an optical axis O of which are the same in size. Accordingly, the first optical element 10, the first spacer 30, the second optical element 20, the second spacer 40, and the image pickup device 50 to which the cover glass 59 has adhered are stacked to adhere to one another, to constitute an image pickup unit 1 which is a rectangular parallelepiped.

While no resin lens is disposed on the first main surface 10SA of the first parallel flat glass 11 composed of optical glass, a resin lens 12 with a negative power is disposed on the second main surface 10SB of the first parallel flat glass 11. A resin lens 22 with a positive power is disposed on a fourth main surface 20SB of the second parallel flat glass 21 composed of optical glass. That is, the first optical element 10 and the second optical element 20 are each a hybrid lens element including a glass base and a resin lens.

A flare aperture 31 is disposed between the first optical element 10 and the first spacer 30, and a brightness aperture 32 is disposed between the first spacer 30 and the second optical element 20. The flare aperture 31 cuts unnecessary light such as ghost or flare.

Note that the flare aperture 31 and the brightness aperture 32 also each have a thickness. Strictly speaking, the distance between the first optical element 10 and the second optical element 20 is defined by the first spacer 30, the flare aperture 31, and the brightness aperture 32.

The flare aperture 31 and the brightness aperture 32 each having a circular opening at its center are manufactured by coating with a metal film using an evaporation method, a sputtering method, or the like, screen printing using a black paint, ink jet printing, or processing of a metal foil, for example.

The image pickup unit 1 has side surfaces all covered with the sealing member 60 composed of an inorganic material, and an optical path space of the image pickup unit for endoscope is a sealed space.

The sealing member 60 is composed of an inorganic material having an oxygen transmission rate and a water vapor transmission rate smaller than the oxygen transmission rate and the water vapor transmission rate of an organic substance such as resin. The sealing member 60 is preferably composed of an inorganic material film such as a silicon nitride film or a silicon oxide film or a metal film, in particular.

Note that if the sealing member 60 is a transparent film, not only a side surface of the image pickup unit 1 but also the first main surface 10SA of the first parallel flat glass 11 may be covered with the sealing member 60. That is, the sealing member 60 may cover at least the side surface of the image pickup unit 1.

The sealing member 60 is disposed on the side surface of the image pickup unit 1 using a sputtering method, a CVD (chemical vapor deposition) method, or a plating method. The thickness of the sealing member 60 is preferably not less than 1 µm nor more than 100 µm. The optical path space can be reliably sealed against oxygen and water vapor if the thickness of the sealing member 60 is the above-described lower limit or more, and the image pickup unit 1 is not prevented from decreasing in diameter if the thickness of the sealing member 60 is the above-described upper limit or less.

If the image pickup unit 1 is disposed in the rigid distal end portion 73A, only the first main surface 10SA of the first parallel flat glass 11 on which no resin lens is disposed becomes an outer surface exposed to the outside. Further, the optical path space where the resin lenses 12 and 22 are disposed is a sealed space blocked from the outside because a side surface of the optical path space is covered with the sealing member 60 composed of an inorganic material. Accordingly, the image pickup unit 1 is superior in reliability, although the image pickup unit 1 includes the lenses 12 and 22 composed of resin inferior in reliability to glass.

The endoscope 9 including the image pickup unit 1 in the rigid distal end portion 73A is superior in reliability, although the endoscope 9 includes the lenses 12 and 22 composed of resin inferior in reliability to an inorganic material.

Figure 5:
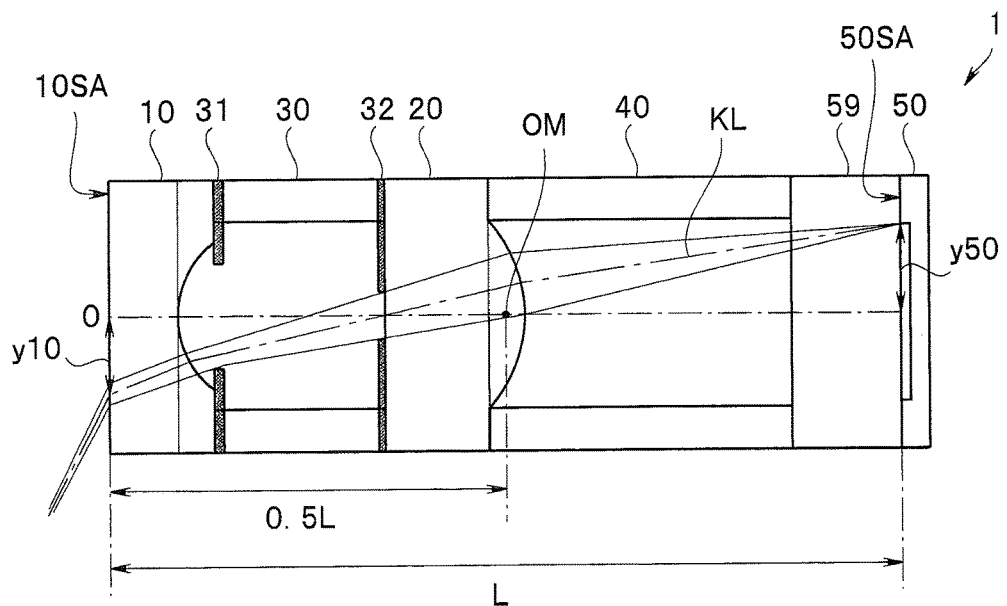
FIG. 5 is an optical path diagram of the image pickup unit according to the present embodiment.

Note that as illustrated in FIG. 5, in the image pickup unit 1, when a middle position of the optical axis O as an optical path between the first main surface 10SA of the first optical element 10 and the light receiving surface 50SA of the image pickup device 50 is taken as OM (a length to the middle position OM is 0.5L with respect to an optical path length L along an optical axis), the brightness aperture 32 is disposed at a position closer to the first main surface 10SA than the middle position OM is. Note that the lens 22 is disposed at a position closer to the image pickup device 50 than the brightness aperture 32 is.

An image height y50 of an image point on the light receiving surface 50SA is substantially the same as or larger than a length y10 from a point at which a main light beam KL which passes through the image point crosses the first main surface 10SA to the optical axis O. That is, an area of the light incidence surface 10SA is substantially the same as or smaller than the area of the light receiving surface 50SA.

The main light beam KL means a light beam which passes through the center of an aperture of an optical system when a bundle of light beams which passes through the optical system is handled.

The image pickup unit 1 in which a disposition position of the optical aperture 31 and the above-described image height are as described above can efficiently image-form the light beam incident from the light incidence surface 10SA on the light receiving surface 50SA, although the image pickup unit 1 is an elongated rectangular parallelepiped, and a shape and a size in cross section perpendicular to the optical axis O of the image pickup unit 1 are respectively the same in any position. That is, the image pickup unit 1 includes an optical system in which an area in cross section in the direction perpendicular to the optical axis of the optical system is substantially the same as or smaller than the area of the light receiving surface 50SA.

The image pickup unit 1 including the second optical member 20 in which the resin lens 22 is disposed on the fourth main surface 20SB is taken as an example in the above-described description. A resin lens may also be disposed on the third main surface 20SA of the second optical member 20, or a resin lens may be disposed on the third main surface 20SA and the fourth main surface 20SB.

Although the image pickup unit 1 including the first optical element 10 and the second optical element 20 has been described as an example, the image pickup unit 1 may further include a third optical element including a resin lens. That is, the respective numbers and configurations of resin lenses, optical elements, spacers, and apertures are not limited to the number and the configuration of image pickup units 1 according to the present embodiment.

However, in the image pickup unit according to the present invention, a configuration in which light which has passed through a resin lens with a negative power is image-formed on a light receiving surface via a resin lens with a positive power, a configuration in which no resin lens is disposed on a light incidence surface (outer surface) of an optical element exposed to the outside, and a configuration in which a side surface is covered with a sealing member 60 composed of an inorganic material are essential.

<Method for Manufacturing Image Pickup Unit>

A method for manufacturing an image pickup unit 1 will be simply described below.

The image pickup unit 1 is a wafer-level image pickup unit manufactured by cutting a bonded wafer obtained by stacking device wafers each having a plurality of functional elements arranged therein in a matrix shape into pieces. A resin adhesive or the like is used to bond the device wafers.

For example, the device wafer in which a plurality of first optical elements 10 are arranged is manufactured by disposing a resin lens 12 on one surface (second main surface) of a glass wafer. Energy curable resin is preferably used as resin composing the resin lens.

When the energy curable resin receives energy of heat, ultraviolet rays, an electron beam, or the like from the outside, crosslinking reaction or polymerization reaction proceeds. Examples of the energy curable resin include transparent ultraviolet curable silicone resin, epoxy resin, and acrylic resin. Note that "transparent" means that a material is hardly light-absorbed or scattered to such an extent that the material can withstand use within a used wavelength range.

The resin lens 12 is manufactured by disposing uncured and liquid-like or gel-like resin on the glass wafer and curing resin for irradiating ultraviolet rays with a mold including concave channels having a predetermined inner surface shape pressed against the resin. Note that silane coupling processing or the like is preferably performed for the glass wafer on which the resin has not been disposed to improve interface adhesion strength between glass and the resin.

An aspherical lens can also be easily manufactured because the inner surface shape of the mold is transferred onto an outer surface shape of the resin lens.

The image pickup unit 1 obtained by being cut into pieces is a rectangular parallelepiped, and adhesive resin or the like is exposed to four side surfaces, each parallel to an optical path as a cut surface, of the image pickup unit 1. An optical path space is sealed with the adhesive resin when the bonded wafer is manufactured. However, the optical path space is not sufficiently sealed with resin which is an organic substance. However, a side surface of the image pickup unit 1 is covered with the sealing member 60 composed of an inorganic material having an oxygen transmission rate and a water vapor transmission rate lower than the oxygen transmission rate and the water vapor transmission rate of the adhesive resin or the like. Accordingly, the sealing of the optical path space is ensured, and oxygen and water are reliably prevented from entering the optical path space.

Although, after the bonded wafer is completely cut into image pickup units 1 as individual pieces, the sealing member 60 may be disposed on a side surface as a flat surface of each of the image pickup units 1, the sealing member 60 is preferably disposed in a state of the bonded wafer. For example, the sealing member 60 can be simultaneously disposed on the respective side surfaces of the plurality of image pickup units 1 by coating a wall surface of a cutting margin of the cut bonded wafer fixed to a dicing tape or the like with the sealing member 60 using a CVD method, a plating method, or the like.

Note that although the image pickup unit 1 is a rectangular parallelepiped, the image pickup unit 1 may be a polygonal column such as a hexagonal column or a circular cylinder by processing at the time of or after cutting.

Modifications to Embodiment

An image pickup unit according to a modification to the image pickup unit 1 according to the present embodiment will be described below. The image pickup unit according to the modification is similar to the image pickup unit 1 and has the same effect as the effect of the image pickup unit 1. Accordingly, components having the same function are respectively assigned the same referee numerals, and hence description of the components is omitted.

<Modification 1>

Figure 6:
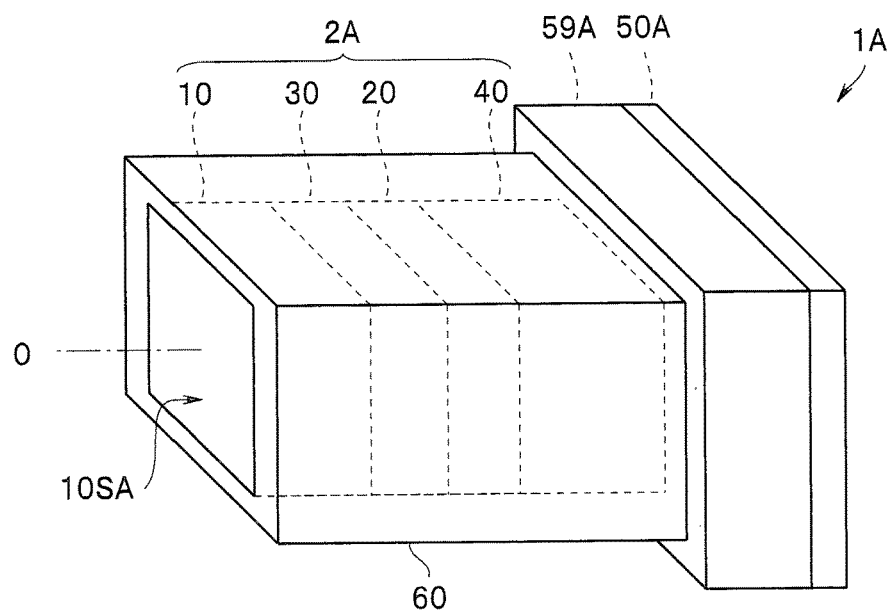
FIG. 6 is a perspective view of an image pickup unit according to a modification 1.

As illustrated in FIG. 6, an image pickup unit 1A according to a modification 1 includes a lens unit 2A including a first optical element 10, a second optical element 20, a first spacer 30, and a second spacer 40 and having a side surface covered with a sealing member 60 composed of an inorganic material and an image pickup device 50A including a cover glass 59A which is larger in size in cross section along an optical axis than the lens unit 2A.

In a method for manufacturing the image pickup unit 1A, an image pickup wafer including a plurality of image pickup devices 50A to which cover glasses 59 have respectively adhered is not stacked when a bonded wafer is manufactured. A plurality of lens units 2A are cur into individual pieces obtained by cutting the bonded wafer, the individual pieces are disposed on the image pickup wafer, and the resultant wafer is cut to obtain image pickup units 1A as individual pieces.

The lens unit 2A is disposed on only the image pickup device 50A, which has been determined to be non-defective by inspection, among the plurality of image pickup devices 50A in the image pickup wafer. Accordingly, the disposed lens unit 2A is prevented from becoming useless. Therefore, the image pickup unit 1A can be produced at lower cost than the image pickup unit 1.

Note that after the image pickup wafer is cut into image pickup devices as individual pieces and the image pickup devices are disposed on the bonded wafer including the plurality of lens units 2A, and then the bonded wafer may be cut into the image pickup units 1A. Further, after the image pickup wafer is cut into image pickup devices as individual pieces, the lens unit 2A may be disposed on each of the image pickup devices. In the cases, the image pickup unit 1A may be an image pickup unit including image pickup devices of a smaller size in cross section along the optical axis than the lens units 2A. That is, the respective sizes in cross section in a direction perpendicular to the optical axis of the image pickup device and the lens unit 2A may be the same, or one of the image pickup device and the lens unit 2A may be larger than the other.

<Modification 2>

Figure 7:
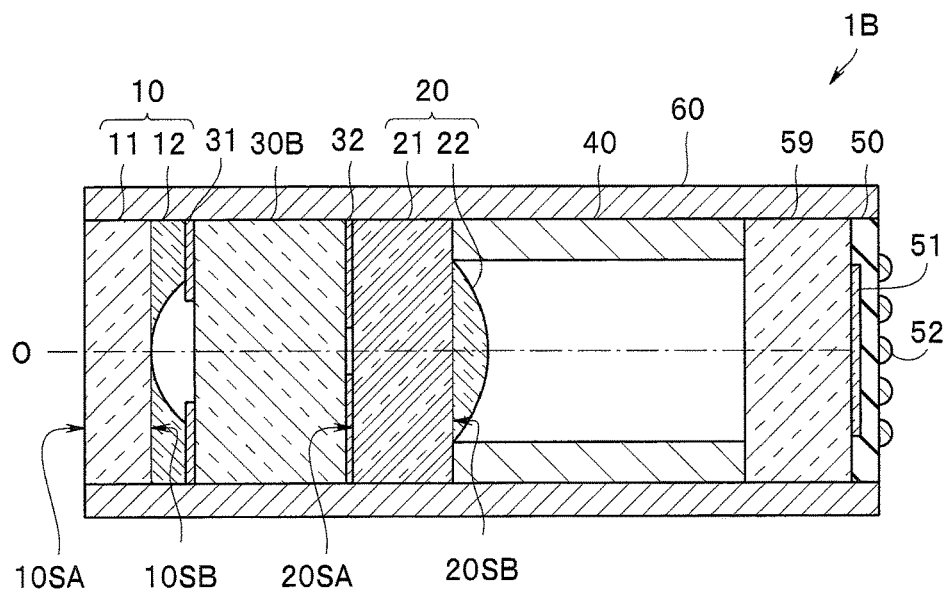
FIG. 7 is a cross-sectional view of an image pickup unit according to a modification 2.

As illustrated in FIG. 7, in an image pickup unit 1B according to a modification 2, a first spacer is an infrared cut filter 30B configured to remove unnecessary infrared rays (e.g., light having a wavelength of 700 nm or more). That is, the infrared cut filter 30B has a spacer function for defining a distance between a first optical element 10 and a second optical element 20 by having a predetermined thickness.

Note that examples of a filter having a spacer function may include a band-pass filter configured to transmit only light having a predetermined wavelength and cut light having an unnecessary wavelength. The second spacer may be a filter, or a part of the spacer may be replaced with a filter.

<Modification 3>

Figure 8:
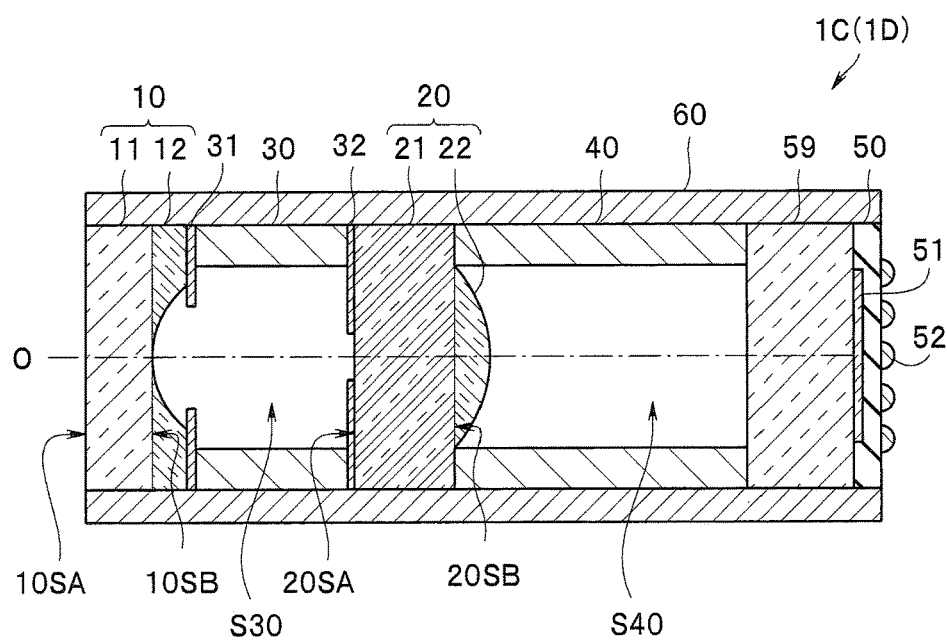
FIG. 8 is a cross-sectional view of respective image pickup units according to modifications 3 and 4.

As illustrated in FIG. 8, a configuration of an image pickup unit 1C according to a modification 3 looks the same as the configuration of the image pickup unit 1. However, in the image pickup unit 1C, respective pressures of optical path spaces S30 and S40 as sealed spaces are each 0.1 atm or less.

In a method for manufacturing the image pickup unit 1C, a bonded wafer is manufactured in a reduced-pressure atmosphere of 0.1 atm or less. A lower limit of pressure is 0.001 atm, for example, from the viewpoint of productivity. Needless to say, respective curved surfaces of resin lenses 12 and 22 are designed such that a light beam is subjected to predetermined refraction in reduced atmospheric pressure.

In the image pickup unit 1C, the resin lenses 12 and 22 do not easily deteriorate because respective oxygen concentrations of the optical path spaces S30 and S40 around the resin lenses are low. Accordingly, the image pickup unit 1C is further superior in reliability to the image pickup unit 1, for example.

<Modification 4>

As illustrated in FIG. 8, a configuration of an image pickup unit 1D according to a modification 4 looks the same as the respective configurations of the image pickup units 1 and 1C. However, in the image pickup unit 1D, optical path spaces S30 and S40 are filled with inert gas above atmospheric pressure. Needless to say, respective curved surfaces of resin lenses 12 and 22 are designed such that a light beam is subjected to predetermined refraction in the inert gas above atmospheric pressure.

In a method for manufacturing the image pickup unit 1D, a bonded wafer is manufactured in inert gas above atmospheric pressure, e.g., in a nitrogen atmosphere of 1.1 atm. An example of the inert gas may be argon, and pressure of the inert gas is preferably not less than 1.01 atm nor more than 2 atm. External gas (air) is less likely to enter the optical path spaces S30 and S40 if the pressure is above the above-described range, and the image pickup unit 1D is easily manufactured if the pressure is below the above-described range.

The image pickup unit 1D is superior in reliability because the possibility that gas (air/water vapor) enters optical path spaces S30 and S40 around the resin lenses from the outside is lower than the possibility in the image pickup unit 1.

Note that an endoscope including each of the image pickup units 1A to 1D according to the modifications 1 to 4 in a rigid distal end portion has an effect of the endoscope 9 and an effect unique to the image pickup unit.

In the image pickup unit in which any one of spacers is a filter, if pressure of an optical path space is 0.1 atm or less or the optical path space is filled with inert gas above atmospheric pressure, needless to say, the image pickup unit also has an effect of the image pickup unit 1C or the image pickup unit 1D.

That is, the present invention is not limited to the above-described embodiments but various changes, combinations, and applications can be made without departing from the scope and spirit of the invention.

What is claimed is:

1. An image pickup unit for endoscope, comprising:
   a first optical element configured to use as a base a first parallel flat glass including a first main surface as a light incidence surface and a second main surface opposing the first main surface;
   a second optical element configured to use as a base a second parallel flat glass including a third main surface and a fourth main surface opposing the third main surface;
   a first spacer configured to define a distance between the first optical element and the second optical element;
   an image pickup device including a light receiving section including a light receiving surface and a rear surface opposing the light receiving surface, the light receiving section being configured such that an object image is formed on the light receiving surface; and
   a second spacer configured to define a distance between the second optical element and the image pickup device, wherein
   the first optical element, the first spacer, the second optical element, and the second spacer, and the image pickup device are stacked, respective outer shapes in cross section in a direction perpendicular to an optical axis of the first optical element, the first spacer, the second optical element, and the second spacer being same in size,
   no resin lens is disposed on the first main surface of the first parallel flat glass and a resin lens with a negative power is disposed on the second main surface of the first parallel flat glass,
   a resin lens with a positive power is disposed on at least one of the third main surface and the fourth main surface of the second parallel flat glass,
   the image pickup unit for endoscope further has side surfaces covered with a sealing member composed of an inorganic material,
   a brightness aperture is disposed between the first optical element and the second optical element, and
   an optical path space of the image pickup unit for endoscope is a sealed space.

2. The image pickup unit for endoscope according to claim 1, further comprising
   a brightness aperture at a position closer to the first main surface than a middle position of an optical path between the first main surface and the light receiving surface, and
   an image height of an image point on the light receiving surface is not less than 90% nor more than 110% of a length from a point at which a main light beam which passes through the image point crosses the first main surface to the optical axis.

3. The image pickup unit for endoscope according to claim 2, wherein an outer shape in cross section in the direction perpendicular to the optical axis of the image pickup device is same in size as the outer shape in cross section in the direction perpendicular to the optical axis of the first optical element.

4. The image pickup unit for endoscope according to claim 2, wherein the first spacer is a filter.

5. The image pickup unit for endoscope according to claim 2, wherein pressure of the sealed space is 0.1 atm or less.

6. The image pickup unit for endoscope according to claim 2, wherein the sealed space is filled with inert gas above atmospheric pressure.

7. An endoscope comprising an image pickup unit for endoscope in a rigid distal end portion of an insertion section, the image pickup unit for endoscope comprising:
   a first optical element configured to use as a base a first parallel flat glass including a first main surface as a light incidence surface and a second main surface opposing the first main surface;
   a second optical element configured to use as a base a second parallel flat glass including a third main surface and a fourth main surface opposing the third main surface;
   a first spacer configured to define a distance between the first optical element and the second optical element;
   an image pickup device including a light receiving section including a light receiving surface and a rear surface opposing the light receiving surface, the light receiving section being configured such that an object image is formed on the light receiving surface; and
   a second spacer configured to define a distance between the second optical element and the image pickup device, wherein
   the first optical element, the first spacer, the second optical element, and the second spacer, and the image pickup device are stacked, respective outer shapes in cross section in a direction perpendicular to an optical axis of the first optical element, the first spacer, the second optical element, and the second spacer being same in size,
   no resin lens is disposed on the first main surface of the first parallel flat glass and a resin lens with a negative power is disposed on the second main surface of the first parallel flat glass,
   a resin lens with a positive power is disposed on at least one of the third main surface and the fourth main surface of the second parallel flat glass,
   the image pickup unit for endoscope further has side surfaces covered with a sealing member composed of an inorganic material,
   a brightness aperture is disposed between the first optical element and the second optical element, and
   an optical path space of the image pickup unit for endoscope is a sealed space.

* * * * *

UNITED STATES PATENT AND TRADEMARK OFFICE
CERTIFICATE OF CORRECTION

| | | |
|---|---|---|
| PATENT NO. | : 10,492,672 B2 | Page 1 of 1 |
| APPLICATION NO. | : 16/181445 | |
| DATED | : December 3, 2019 | |
| INVENTOR(S) | : Noriyuki Fujimori | |

It is certified that error appears in the above-identified patent and that said Letters Patent is hereby corrected as shown below:

On the Title Page

Item (54) and in the Specification at Column 1, Lines 1-2 should read:
IMAGE PICKUP UNIT FOR ENDOSCOPE AND ENDOSCOPE Signed and Sealed this
Third Day of March, 2020

Andrei Iancu
*Director of the United States Patent and Trademark Office*